US006521752B2

(12) United States Patent
Gelling et al.

(10) Patent No.: US 6,521,752 B2
(45) Date of Patent: Feb. 18, 2003

(54) PROCESS TO SEPARATE LINEAR ALKYL 5-FORMYLVALERATE

(75) Inventors: Onko J. Gelling, Stein (NL); Peter C. Borman, Geleen (NL)

(73) Assignees: DSM N.V., Te Heerlen (NL); E.I. Dupont de Nemours and Co., Wilmington, DE (US)

( * ) Notice: Subject to any disclaimer, the term of this patent is extended or adjusted under 35 U.S.C. 154(b) by 0 days.

(21) Appl. No.: 09/930,502

(22) Filed: Aug. 16, 2001

(65) Prior Publication Data

US 2002/0038047 A1 Mar. 28, 2002

Related U.S. Application Data

(63) Continuation of application No. PCT/NL00/00067, filed on Feb. 3, 2000.

(30) Foreign Application Priority Data

Feb. 17, 1999 (EP) .............................................. 99200457

(51) Int. Cl.⁷ ............................................ C07D 201/08
(52) U.S. Cl. ....................................... 540/538; 560/177

(58) Field of Search ................................. 560/174, 177; 540/538

(56) References Cited

U.S. PATENT DOCUMENTS 4,730,041 A * 3/1988 Hutmacher et al. ......... 540/538

FOREIGN PATENT DOCUMENTS

| CA | 2225649 | * | 2/1999 | ......... C07C/69/716 |
| EP | 295551 | | 12/1998 | |
| JP | 56-70097 | * | 6/1981 | ............. C11C/1/10 |
| WO | 9706126 | | 2/1997 | |

* cited by examiner

Primary Examiner—Paul J. Killos
(74) Attorney, Agent, or Firm—Pillsbury Winthrop LLP

(57) ABSTRACT

The invention relates to a process to separate linear 5-formylvalerate compound from a crude mixture comprising 5-formylvalerate compound and 2-, 3- and/or 4-formylvalerate compound by vacuum distillation, wherein the distillation is performed in the presence of a phenolic compound with a boiling point which is at least 10° C. higher than the boiling point of the 5-formylvalerate at 0.1–100 kPa.

14 Claims, 1 Drawing Sheet

PROCESS TO SEPARATE LINEAR ALKYL 5-FORMYLVALERATE

Figure 1:
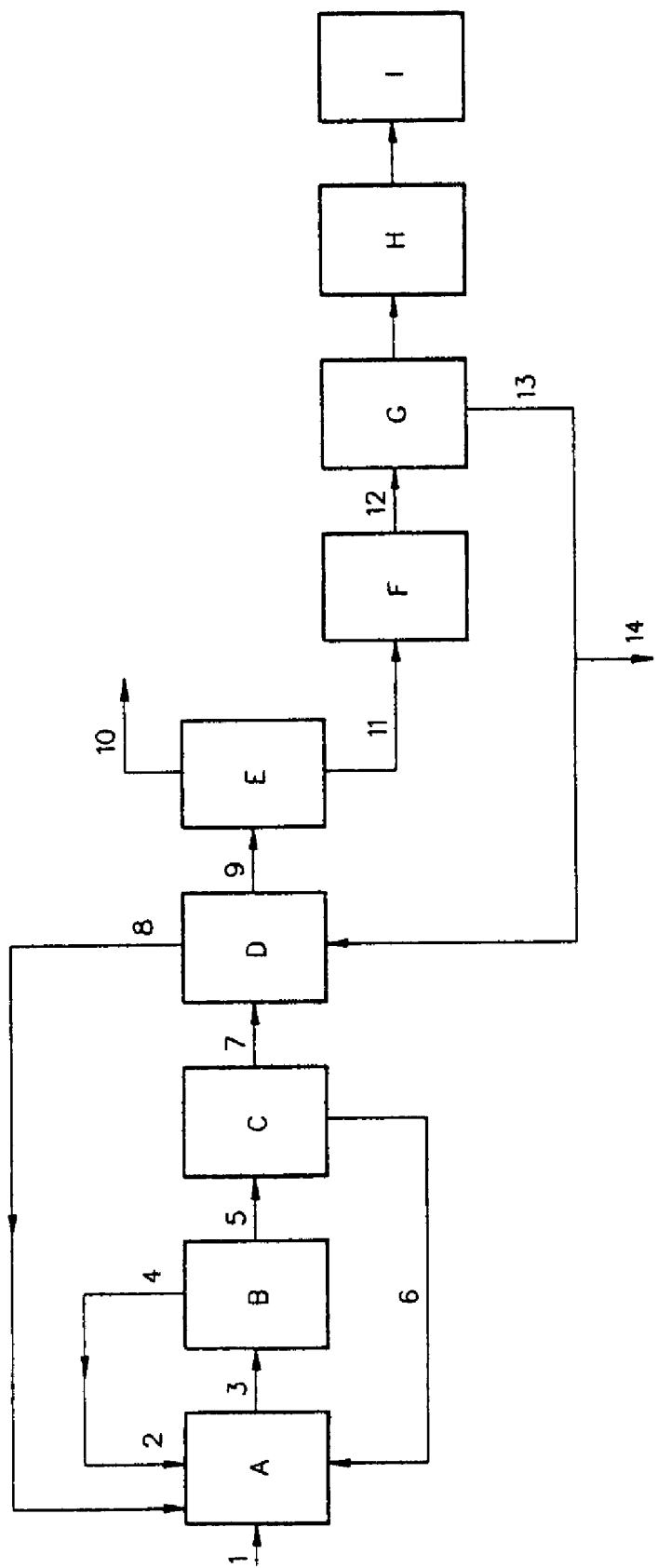

This Application is a continuation of International Application PCT/NL00/00067, filed Feb. 3, 2000, which designated the U.S. and was published in the English language. The entire contents of this PCT application are hereby incorporated by reference.

The invention relates to a process to separate linear 5-formylvalerate compound from a crude mixture comprising 5-formylvalerate compound and 2-, 3- and/or 4-formylvalerate compound by vacuum distillation.

Such a process is described in WO-A-9706126. This patent application describes a process in which the distillation is performed at a low pressure and at a temperature at the bottom of the distillation unit less than 150° C. According to this publication, the presence of a certain amount of oxygen during the distillation is allowed.

A disadvantage of this process is that the ultimate yield of the 5-formylvalerate compound is lowered. This is because a certain amount of the formylvalerate compounds is converted to the corresponding oxidized compounds and because the oxidized compounds in turn initiate the formation of other undesired compounds, for example aldol condensation compounds.

Another disadvantage of this process is that, due to the presence of oxygen, the thus obtained 5-formylvalerate is less suitable to be used as an intermediate to ε-caprolactam. We have found that the presence of oxidized compounds in the 5-formylvalerate product is not acceptable at all. This is because the oxidized compounds will negatively influence the ε-caprolactam quality. Furthermore the oxidized compounds or their derivatives are difficult to remove from ε-caprolactam.

The object of the invention is to minimize the formation of oxidized compounds in the 5-formylvalerate product.

This object is achieved in that the distillation is performed in the presence of a phenolic compound with a boiling point which is at least 10° C. higher than the boiling point of the 5-formylvalerate compound at 0.1–100 kPa.

It has been found that with the process according to the invention the amount of oxidized compounds, for example valerate and/or monoadipate compounds, in the 5-formylvalerate product is considerably reduced compared to the process according to the state of the art. The obtained 5-formylvalerate can be advantageously used to prepare ε-caprolactam. The 5-formylvalerate thus obtained may also be advantageously used as starting compound to prepare other products, for example adipic acid and ε-caprolacton. Another advantage is that the phenolic compound remains in the 5-formylvalerate distillation product, thus reducing oxidation after the distillation as well. In the process according to the invention the phenolic compound is easily separated from the 5-formylvalerate by distillation. The phenolic compound can thus advantageously be reused in for example the process according to the invention.

It was not to be expected that the presence of oxygen during the vacuum distillation of a mixture of 5- and 2-, 3- and/or 4-formylvalerate compound would have such a disadvantageous effect on 5-formylvalerate yield. No mention of this fact is found in the earlier mentioned WO-A-9706126.

EP-A-590613 describes a process for the preparation of a mixture of linear and branched aldehydes by hydroformylating an unsaturated olefin compound in the presence of a rhodium/bidentate phosphite complex catalyst system and an aromatic phenol compound, whereby the catalyst system is separated from the crude aldehyde product by means of distillation. The phenolic compound will be separated from the crude aldehyde product during this separation.

Phenolic compounds, which are employable in the present invention, can be well known compounds which are in general readily commercially available. Any phenolic compound having a boiling point which is at least 10° C. higher than the boiling point of the 5-formylvalerate at 0.1–100 kPa can be used in the process of the invention. Preferably, the phenolic compound has a boiling point which is at least 20° C. higher than the boiling point of the 5-formylvalerate.

Examples of suitable phenolic compounds are 4-hydrophenol (hydroquinone), 3-hydroxyphenol (resorcinol), 1,2,3-trihydroxybenzeen (pyrogallol), 2,6-di-tert.-butyl-4-methylphenol, 6-tert.-butyl-2,4-dimethylphenol, 2,4-dimethyl-6-(tetramethylbutyl)phenol, 2,4-diisoamylphenol, 4,4'-thiodiphenol, the commercially available Irganox-1076, Irganox-1330, Irganox-1010, Irganox-1098, Irganox-1035, Ultranox 210 and Ultranox 276.

Examples of preferred phenolic compounds are the commercially available Irganox compounds.

The process according to the present invention is performed in a vacuum distillation unit comprising one or more distillation columns. In case the vacuum distillation unit contains more than one distillation column, the crude mixture is fed to the first column. The distillation residue of the first column is subsequently fed to a second distillation column. The distilland (vaporized fraction) of the second column is preferably recycled to the first column. The pressure of the vacuum distillation is between 0.1–100 kPa, preferably between 0.1 and 15 kPa. The temperature of the vacuum distallation is between 30 and 250° C., preferably between 30 and 150° C.

The phenolic compound is present in the crude mixture which is fed to the (first) vacuum distillation column or it is added directly to the (first) vacuum distillation column. The phenolic compound can be fed to the distillation column at any point thereof. The phenolic compound is preferably fed to the column above the feed point of the crude mixture of linear and branched formylvalerate compounds. More preferably, the phenolic compound is fed to the top of the column.

The amount of pheholic compound in the mixture is preferably an effective amount sufficient to avoid substantial formation of the undesired byproducts in the 5-formylvalerate stream. In particular, the amount of phenolic compound in the mixture is between 0.01 and 0.2 wt. %, preferably between 0.05 and 0.15 wt. %.

The 5-formylvalerate ester compound can be represented by the following general formula:

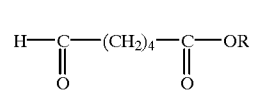

(1)

where R is preferably an organic group with 1 to 20 carbon atoms and more preferably with 1 to 6 carbon atoms. The organic group is an alkyl, cycloalkyl, aryl or aralkyl group. More preferably R is an alkyl group. Examples of R groups include methyl, ethyl, propyl, isopropyl, n-butyl, tert-butyl, isobutyl, cyclohexyl, benzyl and phenyl. By preference R is methyl or ethyl.

In the process according to the invention, the 5-formylvalerate is separated from its branched by-products, 2-, 3- and/or 4-formylvalerate, by vacuum distillation. These branched products can be combusted or decarbonylated to the corresponding pentenoate compound or oxidized to acid compounds like monomethyladipate by well known processes.

The 5-formylvalerate, which is obtained with the process according to the invention, can for example advantageously be used as starting compound for the preparation of adipic acid as described in EP-A-295551. Adipic acid is a precursor for Nylon-6,6.

Another example of an interesting use of the 5-formylvalerate ester compound is the preparation of ε-caprolacton. By reduction of the 5-formylvalerate ester compound and subsequent cyclization of the intermediate compound.

Another example of a very interesting use is the reductive amination of the 5-formylvalerate to an amino intermediate compound and the subsequent cyclisation to ε-caprolactam as for example described in EP-A-729944 and EP-A-234295. ε-caprolactam is a precursor for Nylon-6. The reductive amination may be performed in any suitable solvent in which the 5-formylvalerate compound is soluble. Examples of these solvents are water, ammonia, $C_1$–$C_6$ alkanols, for example methanol, ethanol, propanol or butanol, ethers, for example diethyl ether, methyl tert-butyl ether, dipropylether or diisopropylether.

With reductive amination is meant the reaction of the 5-formylvalerate compound with a molar excess of ammonia and hydrogen. The reductive amination is generally performed in the presence of a group 8–10 metal hydrogenation catalyst, for example Ni, Co, Ru, Pt or Pd. Examples of specific hydrogenation catalysts are Raney nickel, Raney cobalt and supported Ru catalysts for example Ru on carbon or Ru on alumina. Ammonia is present in a 2 to 50 fold molar excess. The pressure is super atmospheric, preferably between 0.5 and 30 MPa. The temperature is generally between 40 and 150° C. The catalyst may for example be present as a slurry or fixed in a packed bed. The reductive amination may for example be performed in a tube reactor or a continuously stirred tank reactor.

The cyclization is carried out in a separate step after the reductive amination. Preferably the catalyst of the reductive amination is not present during the cyclization. The temperature of the cyclization step is generally between 150 and 370° C. and preferably above 260° C. The cyclization may for example be performed in a tube reactor or in a continuously stirred tank reactor. After cyclization of 6-aminocaproate ester to ε-caprolactam, the ε-caprolactam can be separated by for example crystallization or preferably distillation or extraction.

Examples of undesired byproducts which can be formed through oxidation in the process as described in WO-A-9706126, are valerate compounds and monoadipate compounds. These compounds will be converted into amide and/or imide compounds (so-called volatile base compounds) in the above mentioned reductive amination. These volatile base compounds are disadvantageous because they act as chain stoppers in the polymerisation of ε-caprolactam to Nylon-6.

Before the linear 5-formylvalerate compound, which is separated from the crude mixture of linear and branched formylvalerate compounds with the process according to the invention, is entered into the reductive amination section, the phenolic compound is preferably separated from the linear 5-formylvalerate compound by means of distillation. The thus separated phenolic compound is subsequently preferably reused in the process according to the invention.

Other separation techniques, for example extraction and crystallization, are however also possible.

The crude mixture containing linear and branched formylvalerate compounds, which is treated in the process according to the invention, can be obtained with various known processes. For this invention it is not critical how the crude mixture is obtained.

The crude mixture containing linear and branched formylvalerate compounds can, for example, be obtained by esterification of a mixture of 5-formylvaleric acid and 3- and/or 4-formylvaleric acid with an alkanol. The mixture of 5-formylvaleric acid and 3- and/or 4-formylvaleric acid is for example obtained with a process as described in EP-A-742788. As the separation of the linear 5-formylvaleric acid from the mixture of linear and branched formylvaleric acid compounds is generally more difficult to perform than the separation of the linear 5-formylvalerate from a mixture of linear and branched formylvalerate compounds, it is advantageous that the mixture of linear and branched formylvaleric acid compounds is first esterified with an alkanol and subsequently used in the present invention.

The crude mixture containing linear and branched formylvalerate compounds can also be obtained by hydroformylation of a 3-pentenoate compound, 2-pentenoate compound and/or a 4-pentenoate compound. Examples of possible processes are described in the aforementioned WO-A-9706126.

Preferably the hydroformylation is performed using a homogeneous rhodium/bidentate phosphite ligand complex catalyst as for example described in WO-A-9733854 because high selectivities to the desired 5-formylvalerate are achieved. In addition to these disclosed processes heterogeneous hydroformylation catalyst systems may also be used.

The invention is therefore also directed to a process for the continuous preparation of ε-caprolactam, wherein the following steps are performed:

(a) hydroformylation of a 3-pentenoate compound in the presence of a hydroformylation catalyst to a crude mixture comprising linear and branched formylvalerate compounds and unconverted pentenoate compounds, (b) separation of the catalyst from the crude mixture obtained in step (a) and recycling the catalyst to step (a), (c) separation of linear and branched formylvalerate compounds from the unconverted pentenoate compounds, (d) separation of the linear 5-formylvalerate from the crude mixture of linear and branched formylvalerate compounds obtained in step (c) with the process according to the invention, (e) separation of the phenolic compound from the linear 5-formylvalerate compound obtained in step (a) by vacuum distillation at a temperature of 50–200° C. and a pressure of 0.1–100 kPa resulting in a fraction containing the linear aldehyde and a fraction containing the phenolic compound, (f) reuse of the phenolic compound obtained in step (e) in step (d), (g) reductive amination of the linear 5-formylvalerate compound (or derivative thereof) obtained in step (e) to a mixture comprising an amino intermediate compound and ε-caprolactam, (h) cyclisation of the amino intermediate compound mixture obtained in step (g) (or a derivative thereof) to ε-caprolactam at elevated temperature and isolation of ε-caprolactam The 3-pentenoate compound of step (a) may be present as a mixture which also comprises 2- and/or 4-pentenoate compounds.

Preferably, after having separated the phenolic compound from the linear 5-formylvalerate compound in step (e), a part of the fraction containing the phenolic compound is purged and the rest is recycled to step (d).

A preferred embodiment of the invention is a process in which the separation of the linear and branched formylvalerate compounds from the unconverted pentenoate compounds in separation step (c) is performed by means of vacuum distillation in the presence of the phenolic compound. It has been found that the amount of undesired byproducts in the 5-formylvalerate product is further reduced. In this embodiment of the invention, after having separated the phenolic compound from the 5-formylvalerate in separation step (e), the phenolic compound is preferably recycled to separation step (c). It is therefore preferred that in a continuous process for the preparation of $\epsilon$-caprolactam starting with pentenoate compound(s), the separation of the linear and branched formylvalerate compounds from the unreacted pentenoates by means of distillation is performed in the presence of the phenolic compound, and that after having separated the phenolic compound from the 5-formylvalerate product, the phenolic compound is reused in the separation of the linear and branched formylvalerate compounds from the unreacted pentenoates.

In this embodiment of the invention, the phenolic compound is present in the crude mixture of linear and branched formylvalerate compounds and unreacted pentenoates, which is fed to the separation step (c) or it is added directly to the distillation unit in which the separation step (c) is performed. The phenolic compound can be fed to the distillation column at any point thereof. The phenolic compound is preferably fed to the column above the feed point of the crude mixture of unreacted pentenoate compounds and linear and branched formylvalerate compounds. More preferably, the phenolic compound is fed to the top of the column.

FIG. 1 is a schematic representation of a process in which an alkyl 3-pentenoate compound is converted in several steps to $\epsilon$-caprolactam comprising a hydroformylation section (A, B, C and D), a vacuum distillation section according to the invention (E) and a $\epsilon$-caprolactam end section (H and I). FIG. 1 is merely illustrative and is not meant to limit the present invention to this integral process.

In FIG. 1, an alkyl 3-pentenoate is fed to reactor (A) via stream (1). In Reactor A the hydroformylation catalyst system is present. A mixture of CO and $H_2$ is fed to the reactor (A) via stream (2) The effluent of reactor (A) comprising alkyl 5-formylvalerate, alkyl 3-formylvalerate, alkyl 4-formylvalerate, alkyl 2-formylvalerate, low boiling by-products (for example alkylvalerate, alkyl 2-pentenoate and alkyl 4-pentenoate), any unconverted alkyl 3-pentenoate, the catalyst system, carbon monoxide and hydrogen is fed to flasher (B) via stream (3). In the flasher (B) the pressure is reduced to for example atmospheric pressure. Carbon monoxide and hydrogen are separated from the reaction mixture via stream (4) and recycled to the reactor (A). The resulting liquid mixture is fed to separation step (C) via resulting liquid stream (5). In separation step (C) the catalyst system is separated from the liquid mixture, preferably using vacuum distillation. The catalyst system is recycled to reactor (A) via stream (6). The resulting liquid mixture is fed to separation step (D) via stream (7). In separation step (D) the alkyl 5-formylvalerate compound and its branched isomers, alkyl 2-, 3- and 4-formylvalerate compound, are separated from the unreacted alkyl 3-pentenoate compound and double-bound isomers thereof, alkyl 2- and/or 4-pentenoate compounds preferably by means of vacuum distillation at a pressure of 0.1–100 kPa and a bottom temperature of 50–200° C. The unreacted alkyl pentenoate compounds are preferably recycled to reactor (A) via stream (8). Before recycling these compounds, the unconverted alkyl pentenoate compounds are preferably contacted with alumina in order to remove hydroperoxide compounds. These hydroperoxide compounds may be formed as a result of the reaction of oxygen with the alkyl pentenoate compounds. The liquid reaction mixture which resulted from the separation step (D) is via stream (9) fed to the vacuum distillation unit (E), in which the process according to the invention is performed. The mixture containing the branched alkyl 2-, 3- and 4-formylvalerate can be fed to a combustion, decarbonylation or oxydation section via stream (10). The liquid mixture containing the alkyl 5-formylvalerate product and the phenolic compound is optionally stored during some period of time in a storage tank (F). The mixture is fed to this storage tank via stream (11). Before feeding the mixture containing the alkyl 5-formylvalerate product and the phenolic compound, resulting from separation step (E) or leaving the storage tank (F), to the reductive amination section (H) and subsequently to the cyclisation section (I), the mixture is fed via stream (12) to a vacuum distillation unit (G) at a pressure of 0.1–5 kPa in which the phenolic compound is separated from the alkyl 5-formylvalerate product. The separated phenolic compound are recycled via stream (13) to separation step (E) or preferably to separation step (D). Preferably a part of the fraction containing the phenolic compound is purged (stream 14) and the rest is recycled to separation step (E) or (D).

The invention is therefore also directed to a process to separate linear and branched formylvalerate compounds from pentenoate compound(s) by vacuum distillation in the presence of a phenolic compound with a boiling point which is at least 10° C. higher than the boiling point of the linear formylvalerate compound at 0.1–100 kPa.

The invention will be elucidated by the following examples, however these are not intended to limit the scope of the invention in any way. The following abbreviations are used:

M5FV=methyl-5-formylvalerate
M2FV=methyl-2-formylvalerate
M3FV=methyl-3-formylvalerate
M4FV=methyl-4-formylvalerate
MFV=methyl formylvalerates Comparative Experiment A This example serves to determine the degradation rate of M5FV in the presence of oxygen at typical M5FV-distillation temperatures.

In order to simulate typical distillation conditions, 250 g of high purity M5FV (composition see Table I) was heated to 130° C. for 2 hours in a flask. Air was continuously bubbled through the liquid at a rate of 1 Nliter air/hr.kg M5FV. The decomposition was monitored as a function of time by taking samples at regular intervals and subsequent analysis by gas chromatography. The total degradation rate of MSFV was determined to be 3.03 wt %/hr.

TABLE I

| Composition of high purity M5FV | |
|---|---|
| component | wt % |
| methylvalerate | 0.00 |
| monomethyladipate | 0.00 |

TABLE I-continued

Composition of high purity M5FV

| component | wt % |
|---|---|
| M2FV | 0.02 |
| M3EV | 0.08 |
| M4EV | 1.17 |
| M5FV | 98.46 |
| aldol condensates | 0.06 |
| other lights | 0.10 |
| other heavies | 0.11 |

The formation rates of various degradation products are listed in Table II below:

TABLE II

Degradation of M5PV in the presence of oxygen, without Irganox 1010

| Component | wt %/hr |
|---|---|
| Methylvalerate | 1.42 |
| Monomethyladipate | 0.10 |
| aldol condensates | 0.02 |
| other lights | 0.22 |
| other heavies | 1.27 |

It is clear from table II that significant amounts of the typical oxidation products, i.e. methylvalerate and monomethyladipate, were formed.

EXAMPLE I

This example serves to illustrate the stabilizing effect of anti-oxidant Irganox 1010 on M5FV in the presence of oxygen at typical M5FV-distillation temperatures.

In order to simulate typical distillation conditions, 0.2 wt % of Irganox 1010 was added to 250 g of high purity M5FV (composition see Table 1) and heated to 130° C. for 2 hours in a flask. Air was bubbled continuously through the liquid at a rate of 1 Nliter air/hr.kg M5FV. The decomposition was monitored as a function of time by taking samples at regular intervals and subsequent analysis by gas chromatography. The total degradation rate of M5FV was determined to be 1.98 wt %/hr.

The formation rates of various degradation products are listed in Table III below:

TABLE III

Degradation of M5FV in the presence of oxygen and 0.2 wt. % Irganox 1010

| Component | wt %/hr |
|---|---|
| Methylvalerate | 0.65 |
| Monomethyladipate | 0.19 |
| Aldol condensates | 0.02 |
| Other lights | 0.11 |
| Other heavies | 1.01 |

Clearly, the M5FV-degradation rate is much lower in the presence of Irganox 1010 (1.98 wt %/hr vs. 3.03 wt %/hr). More specifically, the formation rate of the typical oxidation product methylvalerate is much lower in the presence of Irganox 1010.

EXAMPLE II

This examples serves to illustrate that oxygen is indeed the major cause for degradation of M5FV at typical M5FV-distillation temperatures.

In order to simulate typical distillation conditions, 0.2 wt % of Irganox 1010 was added to 250 g of high purity M5FV (composition see Table 1) and was heated to 130° C. for 3 hours in a flask. Air was completely excluded from the flask during this period.

The decomposition was monitored as a function of time by taking samples at regular intervals and analysis by gas chromatography. No degradation of M5FV was observed. The same experiment was repeated without the presence of Irganox 1010. Again, no M5FV degradation was observed. Clearly, the presence of oxygen is the most dominating factor in the degradation rate of M5FV at typical distillation temperatures.

What is claimed is:

1. Process to separate linear 5-formylvalerate compound from a crude mixture comprising 5-formylvalerate compound and 2-, 3- and/or 4-formylvalerate compound by vacuum distillation, characterized in that the distillation is performed in the presence of a phenolic compound with a boiling point which is at least 10° C. higher than the boiling point of the 5-formylvalerate at 0.1–100 kPa.

2. Process according to claim 1 wherein the phenolic compound has a boiling point which is at least 20° C. higher than the boiling point of the 5-formylvalerate at 0.1–100 kPa.

3. Process according to claim 1, wherein the phenolic compound is fed to the top of the distillation column.

4. Process according to claim 1, wherein the crude mixture of 5-formylvalerate compound and 2-, 3- and/or 4-formylvalerate compound contains 0.01–0.2 wt. % of the phenolic compound.

5. Process accorddding to claim 4, wherein the crude mixture contains 0.05–0.15 wt. % of the phenolic compound.

6. Process for the continuous preparation of ε-caprolactam, which comprises:
(a) hydroformylation of a 3-pentenoate compound in the presence of a hydroformylation catalyst to a crude mixture comprising linear and branched formylvalerate compounds and unconverted pentenoate compounds,
(b) separation the catalyst from the crude mixture obtained in step (a) and recycling the catalyst to step (a),
(c) separation of linear and branched formylvalerate compounds from the unconverted pentenoate compounds,
(d) separation of the linear 5-formylvalerate from the crude mixture of linear and branched formylvalerate compounds obtained in step (c) vacuum distilling the crude mixture in the presence of a phenolic compound with a boiling point which is at least 10° C. higher than the boiling point of the 5-formylvalerate at 0.1 to 100 kPa,
(e) separation of the phenolic compound from the linear 5-formylvalerate compound obtained in step (a) by vacuum distillation at a temperature of 50–200° C. and a pressure of 0.1–100 kPa resulting in a fraction containing the linear aldehyde and a fraction containing the phenolic compound,
(f) reusing the phenolic compound obtained in step (e) in step (d),
(g) reductively aminating of the linear 5-formylvalerate compound (or a derivative thereof) obtained in step (e) to a mixture comprising an amino intermediate compound and ε-caprolactam, and
(h) cyclising the amino intermediate compound mixture obtained in step (g) (or a derivative thereof) to ε-caprolactam at elevated temperature.

7. Process according to claim 6, wherein the separation of linear and branched formylvalerate compounds from pentenoate compounds in step (c) is performed by vacuum distillation in the presence of the phenolic compound.

8. Process according to claim 6, wherein the separated phenolic compound obtained in step (e) is reused in separation step (c) or (d).

9. Process according to claim 7, wherein the phenolic compound is fed to the top of the distillation column of separation step (c) or (d).

10. Process according to claim 6, wherein, after having separated the phenolic compound from the linear 5-formylvalerate compound in step (e), a part of the fraction containing the phenolic compound is purged and the rest is recycled to step (c) or (d).

11. A process according to claim 1, wherein the formylvalerate compound is a $C_1$–$C_6$ alkyl formylvalerate compound.

12. A process according to claim 11, wherein the alkyl formylvalerate compound is methyl or ethyl formylvalerate.

13. A process to separate linear and branched formylvalerate compounds from pentenoate compound(s) by vacuum distillation in the presence of a phenolic compound with a boiling point which is at least 10° C. higher than the boiling point of the linear formylvalerate compound at 0.1–100 kPa.

14. Process according to claim 6, which further comprises isolating the ε-caprolactam from step (h).

* * * * *